United States Patent
Arlt et al.

(10) Patent No.: US 6,395,780 B1
(45) Date of Patent: May 28, 2002

(54) CLEAVAGE SYSTEM INHIBITORS AS POTENTIAL ANTIPSYCHOTICS

(75) Inventors: Michael Arlt, Seeheim; Gerd Bartoszyk, Weiterstadt, both of (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/559,831

(22) Filed: Apr. 28, 2000

Related U.S. Application Data

(60) Provisional application No. 60/131,647, filed on Apr. 29, 1999.

(30) Foreign Application Priority Data

Apr. 30, 1999 (EP) .............................................. 99108480

(51) Int. Cl.$^7$ ................................................ A61K 31/19
(52) U.S. Cl. ....................................................... 514/557
(58) Field of Search .......................................... 514/557

(56) References Cited

PUBLICATIONS

Abstract to Inoue, F. of "Clincical implications of anticonvulsant induced folate deficiency", from Clin. Pharm., vol. 1, Jul.–Aug., pp. 372–373 (REF 12), 1982.*

* cited by examiner

*Primary Examiner*—Dwayne C. Jones
(74) *Attorney, Agent, or Firm*—Millen, White, Zelano & Branigan, P.C.

(57) ABSTRACT

The invention relates to inhibitors of the glycine cleavage system and their use as potential antipsychotic agents. The invention relates furthermore to a process for treating humans having psychosis, psychosis associated with an illness, schizophrenia, Alzheimers disease or other related psychotic disorders.

4 Claims, 1 Drawing Sheet

CLEAVAGE SYSTEM INHIBITORS AS POTENTIAL ANTIPSYCHOTICS

This application claims the benefit of the filing date of U.S. Provisional Application Serial No. 60/131,647 filed Apr. 29, 1999.

The invention relates to inhibitors of the glycine cleavage system and their use as potential antipsychotic agents. The invention relates furthermore to a process for treating humans having psychosis, psychosis associated with an illness, schizophrenia, Alzheimers disease or other related psychotic disorders.

BACKGROUND AND TECHNICAL FIELD OF THE INVENTION

Glycine is a neurotransmitter in the central nervous system. There, strychnine sensitive glycine receptors exist, where glycine serves as an inhibitory neurotransmitter. In addition there is a glycine binding site located at the NMDA receptor. Here, glycine serves as a excitatory coagonist. For the full activation of the glycine receptor the presence of glutamate and glycine is mandatory. NMDA Antagonists such as phencyclidine (PCP) and related drugs (e.g. ketamine or dizocilpine) induce symptoms in human volunteers which are not distinguishable from schizophrenia (Luby et al., 1959; Rosenbaum et al., 1959; Bakker and Amini, 1961), i.e. they induce a spectrum of symptoms including the positive, negative and cognitive aspects of schizophrenia (Krystal et al., 1994; Mulhotra et al., 1996). In addition, PCP provokes an exacerbation of symptoms in patients suffering from schizophrenia (Lathi et al., 1995; Malhotra et al., 1997). PCP-induced emotional, cognitive and behavioral changes represent not only a clinical model of schizophrenia (Luby et al., 1962), but moreover PCP-induced behavioral changes in mice and rats mimicking the symptoms of schizophrenia in these model organisms are now frequently used animal models for schizophrenia (e.g. Freed et al., 1984) and have been validated with many antischizophrenic drugs with different mechanisms of action (e.g. Jackson et al., 1993; Gleason et al., 1997; Vanover, 1997; Krebs-Thomson et al., 1998). Amongst these animal models utilizing mice and rats, the most prominent models are PCP-induced hyperlocomotion to model the positive and negative symptoms of schizophrenia and PCP-induced disruption of prepulse inhibition revealing the cognition deficit symptoms of schizophrenia.

Glycine, Glycine (Partial) Agonists and Schizophrenia

Glycine and partial agonists at the glycine site have been evaluated in clinical trials (D'Souza 1995). In particular high doses of glycine gave very promising results (Zylberman 1995 and Heresco-Levy 1999). In two double blind, placebo controlled clinical studies it was shown that 0.4 g/kg and 0.8 g/kg glycine given orally along with their usual antipsychotic medication ameliorated negative symptoms by 15% and 30%, respectively. No changes were observed in side effects.

The effects of D-cycloserine were evaluated in several clinical trial. In one clinical trial doses from 15 to 250 mg/d of D-cycloserine were assessed. The results showed that the dose of 50 mg/d reduced negative symptoms in schizophrenic patients (Goff 1995). In another double blind, placebo-controlled clinical trial it was found that 50 mg/d along with their effective dose of antipsychotics gave an improvement in negative symptoms (Goff 1999).

Glycine and the Glycine Cleavage System

Glycine is not only a neurotransmitter but also one of the major sources of C-1 building blocks. It is catabolized by the Glycine Cleavage System (GCS) to yield carbon dioxide, ammonia and methylene tetrahydrofolate.

The GCS consists of four enzymes:
glycine decarboxylase, P-protein,
hydrogen carrier protein, H-protein
aminomethyltransferase, T-protein,
dihydrolipoamide dehydrogenase, L-protein, The following reaction scheme applies (Kikuchi 1980):

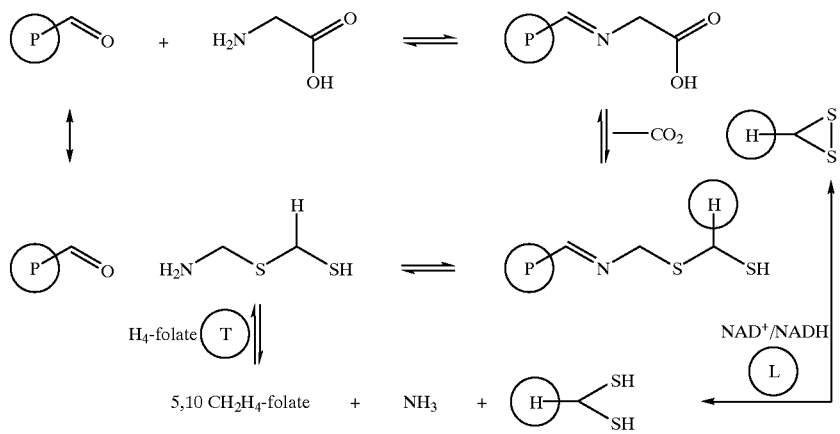

In vitro it is possible to substitute the H-protein with lipoic acid (Hiraya 1980).

SUMMARY OF THE INVENTION

The invention relates to inhibitors of the glycine cleavage system and their use as potential antipsychotic agents. It could be shown that, for example, valporate and cysteamine are potential inhibitors. The invention relates furthermore to a process for treating humans having psychosis, psychosis associated with an illness, schizophrenia, Alzheimers disease or other related psychotic disorders.

Therefore, it is an object of the invention to provide a process for treating a psychotic disorder in a human patient which comprises administering to said human a sufficient amount of an inhibitor, preferably valporate and/or cysteamine, of the glycine cleavage system.

In detail, the invention provides a process, wherein the psychotic disorder is schizophrenia, major depression, manic-depressive disorder, Alzheimers disease or post-traumatic stress syndrome.

Furthermore, the invention provides a process, wherein administering the glycine cleavage system inhibitor affects augmenting NMDA receptor-mediated neurotransmission.

DESCRIPTION OF THE INVENTION

Distribution

Figure 1A:
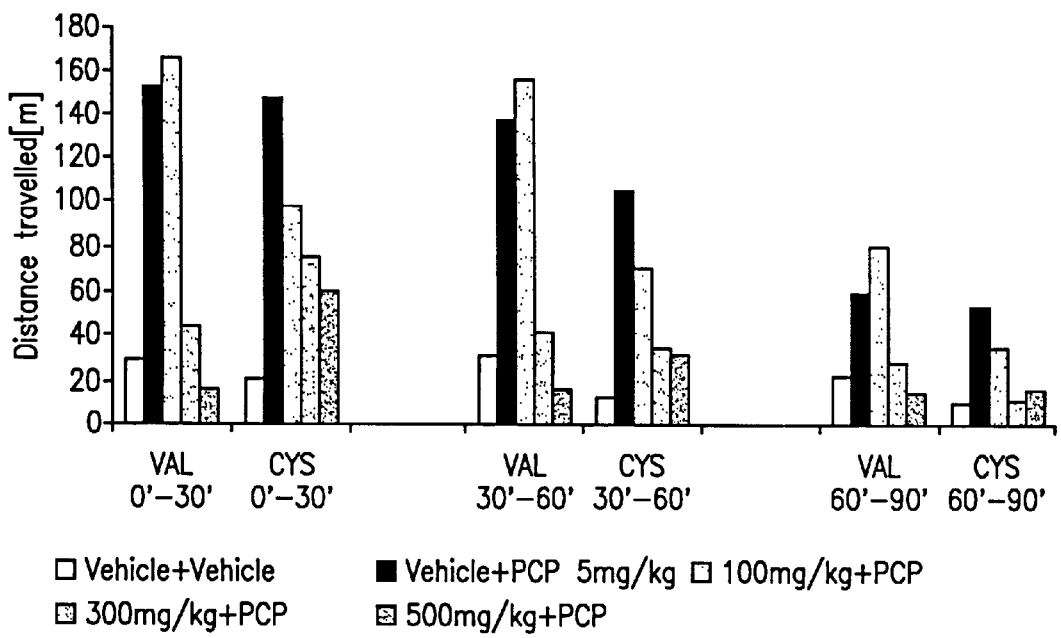
FIG. 1 shows the reduction of PCP-induced hyperlocomotion with the administration of valproate and cysteamine.

In chicken GCS activity was found in liver, kidney and brain but not in heart or spleen. P-protein mRNA was found in liver, kidney and brain, T- and H-protein activity appeared additionally in kidney and heart. In the rat brain H- and T-protein mRNA were found in olfactory bulb, cerebrum, hippocampus, cerebellum, brainstem and spinal cord. P-protein mRNA was abundant in olfactory bulb, cerebrum, hippocampus and cerebellum. This parallels the distribution of NMDA receptors (Kure 1997).

P-Protein

The P-protein was characterized from chicken liver (1500 g of liver yielded 8 mg of protein corresp. to 33.000 U). Its molecular weight is 208.000. It is a homodimer, each monomer carrying one molecule of pyridoxalphosphate (Hiraya, 1980). The monomers of the chicken and human P-protein have been cloned. Structural homology is 84. Disregarding changes Asp→Glu, Arg→Lys and Ser→Thr strucural homology is as high as 93% (Kume 1991). The homology between the chicken and the *E. Coli* enzyme is 53% (Kure 1997).

Known Inhibitors of the Glycine Cleavage System and Activity in Animal Models

Valproate (anticonvulsive drug, EMD 49461) is known to inhibit the GCS (Martin-Gallardo 1985). The Ki is 0.59 mM, 2 mM in liver and brain mitochondria, respectively. I.p. administration of 720 mg/kp in rats resulted in an elevation of glycine levels in blood, liver, brain and spinal cord to appr. 140% of control rats. Cysteamine (EMD 247 714) is an known GCS inhibitor (IC50 appr. 60?M, Lowry 1986). I.p. administration of 250 mg/kg Cysteamine in 8 day old rats caused an increase of glycine in the cortex to 360% of the control animals (Iwama 1997). Other weak inhibitors are aminoacetonitrile and propargylamine (Benavides 1983).

For the PCP-induced hyperlocomotion model we use a test apparatus consisting of a clear plexiglass box (45 cm×45 cm) equipped with two series of equally spaced infrared beam lights controlling X-Y axes and connected to a microcomputer. Measured automatically are the distance (way) traveled [m], and the time spent with locomotion or resting [sec] in intervals of 30 min over a total of 90 minutes following PCP administration. The known model substances for inhibition of the glycine cleavage system, valproate and cysteamine, are administered parenterally before the PCP challenge (PCP 5 mg/kg administered intraperitoneally). PCP at the indicated dose induces excessive locomotor behavior with an increase of about 200–250% measured by either locomotion distance or time compared to control animals. Valproate and cysteamine were used at doses from 100 to 500 mg/kg. Both valproate and cysteamine reduce PCP-induced hyperlocomotion at various doses tested (see figures) indicating an antischizophrenic action.

Only limited data is available for the only more recently established model of PCP-induced disruption of prepulse inhibition (PPI). To our knowledge, only the glycine agonist R-(+)-HA-966 and the glycine transporter antagonists D-cycloserine have so-far investigated and demonstrated a reversal of PCP-induced PPI (Kretschmer and Koch, 1997; Furuya et al., 1998). In the hyperlocomotion model with PCP or related drugs used as challenge stimulants, the efficacy of glycine itself, the glycine agonist R-(+)-3-amino-1-hydroxypyrrolid-2-one (R-(+)-HA-966), the partial agonist D-cycloserine or the glycine transporter antagonist glycyldodecylamide (GDA) have been repeatedly demonstrated in rodents (e.g. Toth and Lajtha, 1986; Toth et al., 1986; Singh et al., 1990; Kretschmer et al., 1992; Carlsson et al., 1994; Javitt et al., 1997; Nilsson et al., 1997; Javitt et al., 1999).

For the PCP-induced disruption of PPI we use a commercially available standard equipment (Coulbourn Instruments, USA) consisting of a sound attenuated test box equipped with a startle response measuring unit connected to a microcomputer; a white noise generator applies a constant level of back ground noise during the experiment. After a habituation period, a series of 70 combinations of prepulses (no prepulse or 8 to 6 dB above back ground noise) and pulses (90 to 126 dB) is randomly applied to the rats. The known model substances for inhibition of the glycine cleavage system, valproate and cysteamine, are administered parenterally before the PCP challenge (PCP 1–5 mg/kg administered subcutaneously). In control animals, presentation of the prepulse inhibits the startle response elicited by the pulse alone. PCP at the indicated doses induces a disruption of PPI by a maximum of about 70% compared to control animals. The doses indicated above are used for valproate and cysteamine, administered before the PCP challenge. Both valproate and cysteamine reverse PCP-induced disruption of PPI at different prepulse/pulse combinations at various doses tested indicating an antischizophrenic action.

Although the complex interaction of glycine with the neurotransmitter dopamine is not yet fully understood, the counterbalancing effects (symmetric bilateral changes) of glycine and dopamine, at least in part via GABAergic and cholinergic interneurons, in the central nervous system are well known for long (e.g. Cheramy et al., 1978; Giorguieff et al., 1979; Leviel et al., 1979; Schmidt and Kretschmer, 1997; Nankai et al., 1998). Dopamine antagonists are the classic antischizophrenic drugs, and conventional animal models to test for antischizophrenic drugs with a dopaminergic mechanism of action use the induction of stereotyped behaviours such as climbing behavior in mice by the application of dopamine-agonistic drugs such as apomorphine (Protais et al., 1976; Puech et al., 1978).

Using the climbing test in mice, we previously found that the glycine transporter inhibitor GDA and the partial glycine agonist D-cycloserine inhibited apomorphine (1.25 mg/kg administered subcutaneously)-induced climbing behavior in mice.

Therefore the model compound cysteamine at the doses indicated before are investigated in the climbing test in mice, too. Surprisingly again, cysteamine when given prior to the apomorphine challenge inhibit apomorphine-induced climbing at various doses with an ED50 value (dose which inhibits apomorphine-induced climbing by 50%) of 500 mg/ kg further indicating an antischizophrenic action.

From these findings it is suggested to use inhibitors of the glycine cleavage system directly for the treatment of psychotic disorders like schizophrenia, schizoid or schizotypal personality disorders, disorders associated with psychosis such as major or manic depression, Alzheimers disease and post-traumatic stress syndroms. The inhibitors can be adminstered alone or together with usual antipsychotic drugs.

Figure 1B:
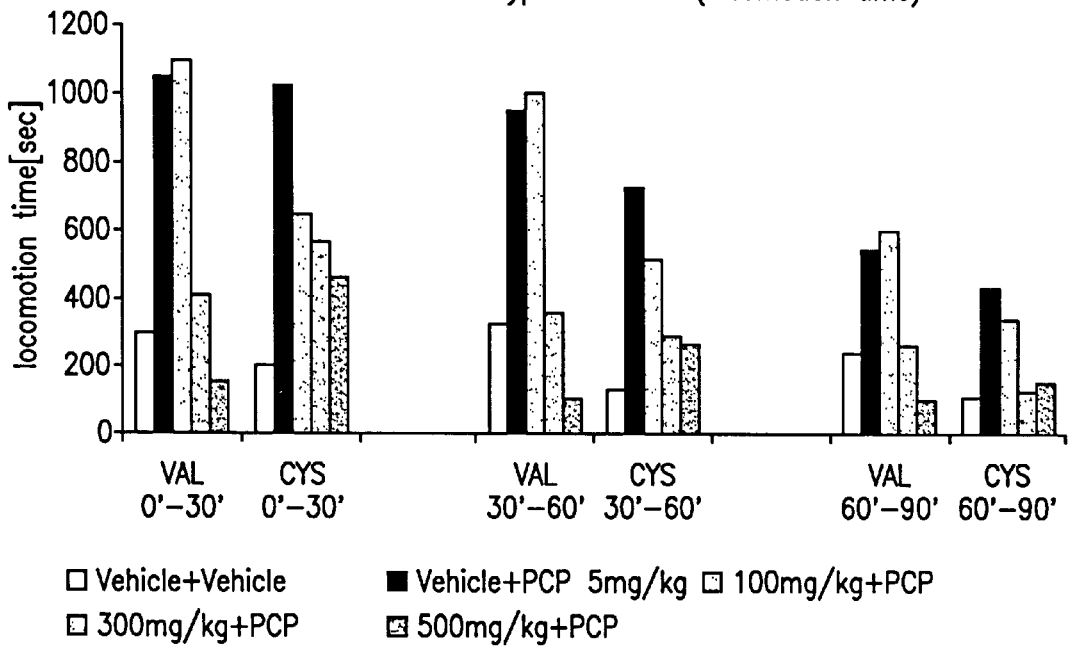

FIG. 1A depicts the effect of valproate (VAL) and cysteamin (CYS) on PCP induced hyperlocomotion, on the distance traveled, and FIG. 1B depicts the effect of valproate (VAL) and cysteamin (CYS) on PCP induced hyperlocomotion, on the locomotion time.

LITERATURE

Bakker and Amini, Compr. Psychiatry 2, 1961, 269.
Benavides J., et al., Biochem. Pharmacol. 32, 1983, 287.
Carisson et al., J Neural Transm-Gen Sect 95, 1994, 223.
Cheramy et al., Eur J Pharmacol 47, 1978, 141.
D'Souza D. C. et al., CNS Drugs Rev. 1, 1995, 227.
Freed et al., Neuropharmacology 23, 1984, 175.
Furuya et al., Brain Res 781, 1998, 227.
Giorguieff et al., J Physiol 75, 1979, 611.
Gleason et al., Psychopharmacology 129, 1997, 79.
Goff D. C. et al., Arch. Gen. Psychiatry 56,1999, 21.
Goff, D. C. et al., Am. J. Psychiatry. 152, 1995, 1213.
Heresco-Levy U., Arch. Gen. Psychiatry 56, 1999, 29.
Hiraya et al., J. Biolog. Chem. 255, 1980, 11664.
Iwama H., et al., Biochem. Biophys. Res. Commun. 231, 1997, 793.
Jackson et al., Pharmacol Biochem Behav 48, 465.
Javitt et al., Biol Psychiatry 45, 1999, 668.
Javitt et al., Neuropsychopharmacology 1997, 17, 202.
Kikuchi Goro, et al. Biochem. Soc. Transactions, 1980, 504.
Krebs-Thomson et a., Neuropsychopharmacology 18, 1998, 339
Kretschmer and Koch, Psychopharmacology 130, 1997, 131.
Kretschmer et al., J Nezral Transm 87, 1992, 23.
Krystal et al., Arch Gen Psychiatry 51, 1994, 199.
Kume A., et al., J. Biolog. Chem. 266, 1991, 3323.
Kure S., et al., Jpn. J. Human Genet., 42, 1997, 13.
Lathi et al., Neuropsychopharmacology 13, 1995, 9.
Leviel et al., Brain Res 175, 1979, 259.
Luby et al., Am J Psychiatry 119, 1962, 61.
Luby et al., Arch Neurol Psychiatry 81, 1959, 363.
Malhotra et al., Neuropsychopharmacology 14, 1996, 301.
Malhotra et al., Neuropsychopharmacology 17, 1997, 141.
Martin-Gallardo, et al., Biochem. Pharmacol. 34, 1985, 2877.
Nankai et al., Prog Neuropsychopharmacol Biol Psychiatry 22,1998, 35.
Nilsson et al., J Neural Transm 104, 1997, 1195.
Pratais et al., Psychopharmacology 50, 1976, 1.
Puech et al., Eur J Pharmacol 50, 1978, 291.
Rosenbaum et al., Arch Gen Psychiatry 1, 1959, 651.
Schmidt and Kretschmer, Neurosci Biobehav Rev 21, 1997, 381.
Singh et al., Proc Natl Acad Sci USA 87, 1990, 347.
Toth and Lajtha, Neurochem Res 11, 1986, 393.
Toth et al., Res Commun Psychol Psychiatry Behav 11, 1986, 1.
Vanover, Eur J Pharmacol 332, 1997, 115.
Zylberman I. et al., N.Y. Acad. Sci. 757, 1995, 487.

The entire disclosure of all applications, patents and publications, cited above, and of corresponding U.S. Provisional application No. 60/131,647, filed Apr. 29, 1999, is hereby incorporated by reference.

What is claimed is:

1. A method for treating a psychotic disorder in a human patient which comprises administering to said human a sufficient amount of an inhibitor of the glycine cleavage system.

2. The method of claim 1 wherein the psychotic disorder is schizophrenia, major depression, manic-depressive disorder, Alzheimer's disease or post-traumatic stress syndrome.

3. The method of claim 2 wherein administering the glycine cleavage system inhibitor affects augmenting NMDA receptor-mediated neurotransmission.

4. A method of claim 1, wherein the inhibitor of the glycine cleavage system is valporate or cysteamine.

* * * * *

UNITED STATES PATENT AND TRADEMARK OFFICE
CERTIFICATE OF CORRECTION

PATENT NO.    : 6,395,780 B1
DATED         : May 28, 2002
INVENTOR(S)   : Arlt et al.

It is certified that error appears in the above-identified patent and that said Letters Patent is hereby corrected as shown below:

<u>Title page,</u>
Item [54], Title, before "CLEAVAGE" insert -- GLYCINE --.

Signed and Sealed this

Eighteenth Day of February, 2003

JAMES E. ROGAN
*Director of the United States Patent and Trademark Office*